United States Patent
Johnson

(10) Patent No.: US 10,052,193 B2
(45) Date of Patent: Aug. 21, 2018

(54) SYNTHETIC FLAP FOR TRABECULECTOMY PROCEDURES

(71) Applicant: Novartis AG, Basel (CH)

(72) Inventor: Andrew David Johnson, Laguna Niguel, CA (US)

(73) Assignee: Novartis AG (CH)

(*) Notice: Subject to any disclaimer, the term of this patent is extended or adjusted under 35 U.S.C. 154(b) by 130 days.

(21) Appl. No.: 15/238,330

(22) Filed: Aug. 16, 2016

(65) Prior Publication Data
US 2018/0049865 A1   Feb. 22, 2018

(51) Int. Cl.
| A61F 2/14 | (2006.01) |
| A61F 9/007 | (2006.01) |
| A61F 9/00 | (2006.01) |
| A61F 9/008 | (2006.01) |
| A61M 27/00 | (2006.01) |

(52) U.S. Cl.
CPC ............ *A61F 2/142* (2013.01); *A61F 9/0017* (2013.01); *A61F 9/00781* (2013.01); *A61F 2009/00891* (2013.01); *A61M 27/002* (2013.01)

(58) Field of Classification Search
CPC .......................... A61F 9/0017; A61F 9/00781
See application file for complete search history.

(56) References Cited

U.S. PATENT DOCUMENTS

| 5,346,464 A * | 9/1994 | Camras ............... A61F 9/00781 604/294 |
| 5,601,094 A * | 2/1997 | Reiss .................. A61F 9/00781 128/899 |
| 5,702,414 A * | 12/1997 | Richter ............... A61F 9/00781 606/108 |
| 5,879,319 A * | 3/1999 | Pynson ............... A61F 9/00781 604/8 |
| 7,207,965 B2 * | 4/2007 | Simon ................. A61F 9/00781 604/8 |
| 2005/0085905 A1 * | 4/2005 | Weiner ................. A61F 9/0017 623/4.1 |
| 2011/0245753 A1 * | 10/2011 | Sunalp ............... A61F 9/00781 604/9 |
| 2012/0226132 A1 * | 9/2012 | Wong ....................... A61B 3/16 600/398 |
| 2013/0158381 A1 * | 6/2013 | Rickard .................... A61B 3/16 600/399 |
| 2013/0317411 A1 * | 11/2013 | Agarwal ............. A61F 9/00781 604/8 |

* cited by examiner

*Primary Examiner* — David H Willse
*Assistant Examiner* — Javier Blanco
(74) *Attorney, Agent, or Firm* — Kenneth D. Bassinger

(57) ABSTRACT

A method includes forming a conjunctival incision in a patient's eye, attaching a synthetic flap to the patient's eye within the conjunctival incision, forming a scleral tunnel underneath the synthetic flap, the scleral tunnel extending from an exterior of a sclera to an anterior chamber of the patient's eye, and closing the conjunctival incision.

6 Claims, 4 Drawing Sheets

SYNTHETIC FLAP FOR TRABECULECTOMY PROCEDURES

TECHNICAL FIELD

The present disclosure is directed to devices and methods for performing ophthalmic surgical procedures, and more particularly, to methods and devices used in trabeculectomy procedures.

BACKGROUND

Glaucoma, a group of eye diseases affecting the retina and optic nerve, is one of the leading causes of blindness worldwide. Most forms of glaucoma arise as a result of highly elevated intraocular pressure (TOP) sustained over prolonged periods of time. In some instances, increases in TOP are a result of high resistance to drainage of the aqueous humor relative to its production. Left untreated, an elevated TOP can cause irreversible damage to the optic nerve and retinal fibers resulting in a progressive, permanent loss of vision.

Trabeculectomy procedures are often used to treat Glaucoma. Such procedures typically involve cutting a flap out of the patient's sclera and forming a scleral tunnel that extends from underneath the flap to the anterior chamber of the patient's eye. The tunnel provides a flow-path for fluid from the anterior chamber of the patient's eye to flow into the space surrounding the flap.

Cutting the flap into the sclera is a challenging and delicate process requiring skill and practice. The thickness of the flap can vary greatly depending on the skill level of the surgeon, and may vary greatly from surgery to surgery even among skilled surgeons. The variation in the thickness of the flap among different surgeries and different surgeons leads to inconsistent outcomes of the trabeculectomy procedure. In some procedures, surgeons may inadvertently sever part of the sclera when attempting to cut the scleral flap, subjecting the patient to additional trauma. To avoid these variances in procedures and outcomes, it is desirable to have improved methods and devices used in trabeculectomy procedures.

SUMMARY

According to one example, a method includes forming a conjunctival incision in a patient's eye, attaching a synthetic flap to the patient's eye within the conjunctival incision, forming a scleral tunnel underneath the synthetic flap, the scleral tunnel extending from an exterior of a sclera to an anterior chamber of the patient's eye, and closing the conjunctival incision.

According to one example, a method includes attaching an edge of a synthetic flap to a patient's eye within a conjunctival incision, the synthetic flap having a first dimension within a range of 3-7 millimeters, a second dimension within a range of 3-7 millimeters, and a third dimension within a range of about 0.5 to 1.5 millimeters. The second dimension is substantially perpendicular to the first dimension and the third dimension is substantially perpendicular to both the first and second dimensions. The method further includes forming a scleral tunnel underneath the synthetic flap, the scleral tunnel extending from an exterior of a sclera to an anterior chamber of the patient's eye.

According to one example, a synthetic flap for use in a trabeculectomy procedure includes a polymer sheet material sized and shaped to be inserted into a conjunctival incision. The polymer sheet material includes a first dimension ranging in length between 3 and 7 millimeters and a second dimension ranging in length between 3 and 7 millimeters. The second dimension is perpendicular to the first dimension. The polymer sheet material includes an attachment feature extending along a length of an edge of the polymer sheet material. The attachment feature is arranged to secure the polymer sheet material to a sclera of a patient's eye. The polymer sheet material further includes a thickness within a range of 0.5 to 1.5 millimeters.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
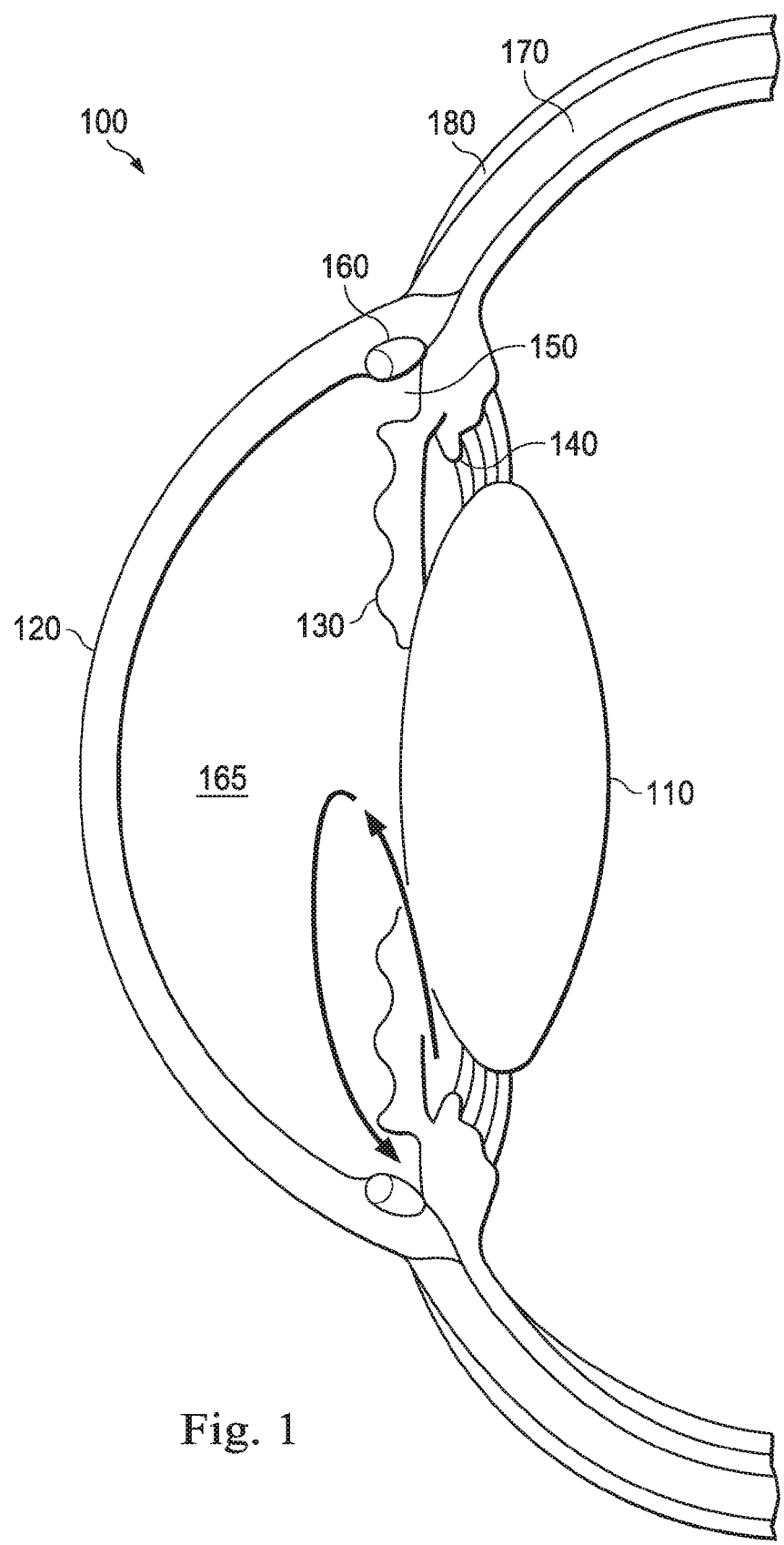
FIG. 1 is a diagram showing an illustrative eye according to one example of principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to a synthetic flap for use in trabeculectomy procedures. Such a flap may be used in place of the conventional surgically-carved flap of patient tissue, possibly reducing reliance on the skill and experience of a particular surgeon and providing a more repeatable, predictable surgical treatment. This of course may lead to better patient outcome. In some examples, the synthetic flap may be formed of a small, thin, flexible sheet of material. Although flap sizes may vary, some flap implementations may be substantially square shaped and have dimensions of 5×5 millimeters. Some flap implementations may be about 1 millimeter thick. These dimensions however are non-limiting and other dimensions and thicknesses are contemplated as well. Some implementations of the flap include an attachment feature such as, for example, an adhesive portion or textured portion that sticks to the patient's eye. The attachment feature may be placed along one edge of the synthetic flap or along multiple edges.

To use such a synthetic flap for a trabeculectomy procedure, an incision is made in the conjunctiva. Depending on the implementation, the synthetic flap may then be inserted into the conjunctival incision into the space between the conjunctiva and the patient's sclera. The synthetic flap may then be attached to the outer surface of the sclera. This may be done using the attachment feature of the synthetic flap. Additionally, a scleral tunnel may be formed underneath the synthetic flap. The scleral tunnel may allow fluid to flow from the anterior chamber to the space underneath the synthetic flap. In some examples, the corners of the synthetic flap opposite the attachment feature can be connected to the sclera. This may control the fluid flow from underneath the flap into the space within the conjunctival incision.

Using the synthetic flap as described herein provides various advantages not obtained using conventional procedures. For example, surgeons of varying skill levels may create a consistent, repeatable flow drainage path. This may make surgical outcomes more predictable. Additionally, the trabeculectomy procedure may be less invasive for the patient. Furthermore, the synthetic flap may be made of an anti-fibrotic material to reduce scarring and prolong the efficacy of the trabeculectomy procedure.

FIG. 1 is a diagram of the front portion, or anterior segment of an eye 100. FIG. 1 shows representations of the lens 110, cornea 120, iris 130, ciliary body 140, trabecular meshwork 150, Schlemm's canal 160, and anterior chamber 165. Anatomically, the anterior segment of the eye includes the structures that cause elevated TOP which may lead to glaucoma.

Aqueous humor fluid is produced by the ciliary body 140 that lies beneath the iris 130 and adjacent to the lens 110 in the anterior segment of the eye. This Aqueous humor fluid washes over the lens 110 and iris 130 and flows to the drainage system located in the angle of the anterior chamber 165. The angle of the anterior chamber 165, which extends circumferentially around the eye, contains structures that allow the aqueous humor fluid to drain.

The trabecular meshwork 150 is commonly implicated in glaucoma. The trabecular meshwork 150 extends circumferentially around the anterior chamber. The trabecular meshwork 150 may act as a filter, limiting the outflow of aqueous humor and providing a back pressure that directly relates to TOP.

Schlemm's canal 160 is located beyond the trabecular meshwork 150. The Schlemm's canal 160 is fluidically coupled to collector channels (not shown) allowing aqueous humor fluid to flow out of the anterior chamber 165. The two arrows in the anterior segment shown in FIG. 1 show the flow of aqueous humor fluid from the ciliary bodies 140, over the lens 110, over the iris 130, through the trabecular meshwork 150, and into the Schlemm's canal 160 and its collector channels.

FIG. 1 also shows a sclera 170 and a conjunctiva 180. The sclera 170 is the opaque, fibrous, protective, outer layer of the eye, and may be referred to as the "white the eye". Covering the sclera 170 as well as part of the inside of the eyelids is the conjunctiva 180. The conjunctiva 180 helps lubricate the eye by producing mucus and tears.

When the aqueous humor fluid fails to drain properly, it can increase the pressure within the eye, leading to various complications. One procedure to help alleviate the intraocular pressure is to perform a trabeculectomy procedure. As described above, a trabeculectomy procedure conventionally involves incising the conjunctiva 180 to form a space between the conjunctiva and the sclera 170. Then, a flap is cut into the sclera 170, and a scleral tunnel is formed underneath that flap. The scleral tunnel extends from the space underneath the flap into the anterior chamber 165, thus allowing aqueous humor fluid to flow through. However, as described above, such a scleral flap may be difficult to cut because it requires such precise, delicate operations and therefore, is often cut inconsistently among procedures.

Figure 2:
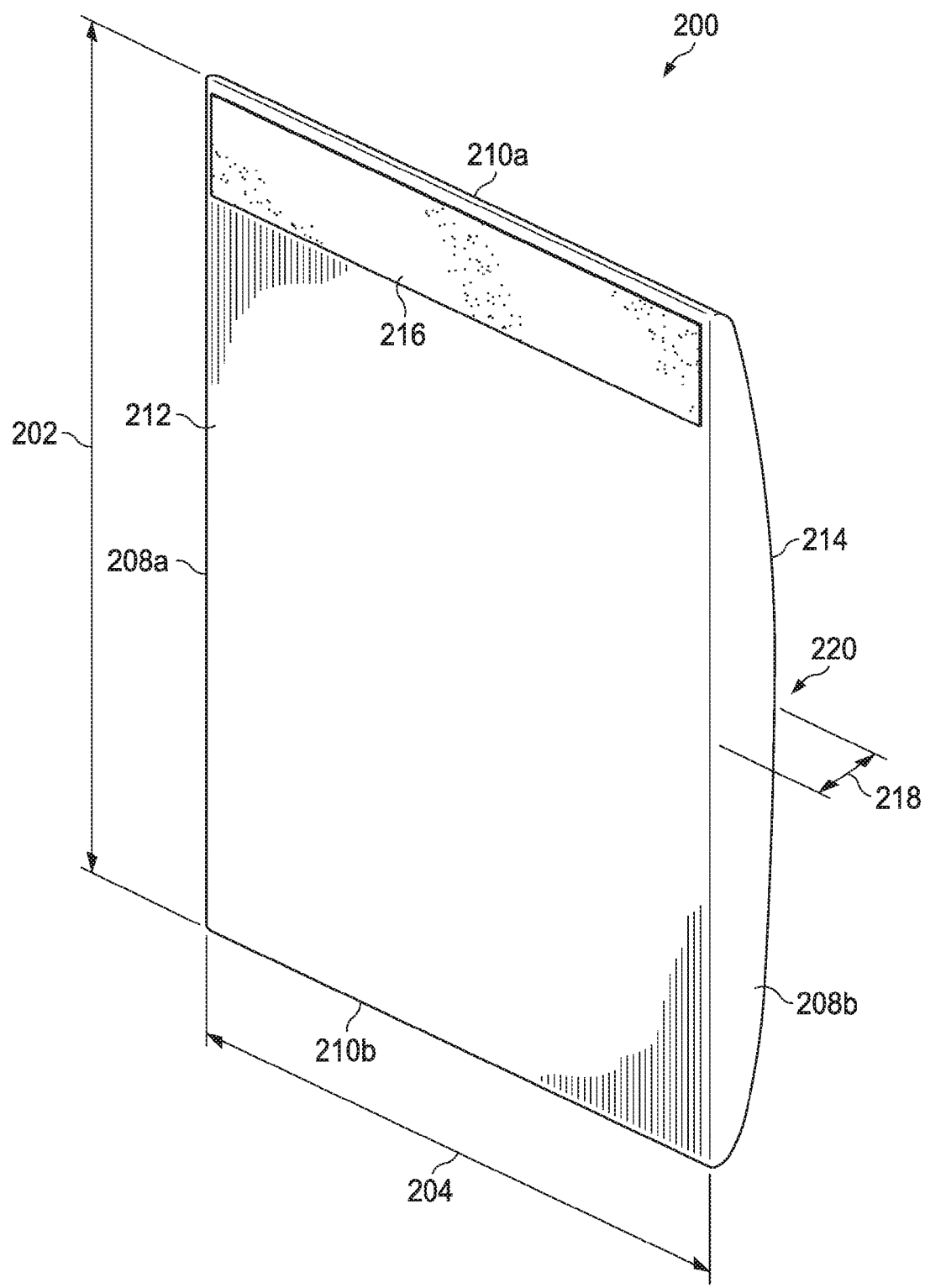
FIG. 2 is a diagram showing an illustrative synthetic flap for use in trabeculectomy procedures according to one example of principles described herein.

FIG. 2 shows an illustrative synthetic flap 200 for use in trabeculectomy procedures. According to the present example, the synthetic flap 200 is a small, thin, flexible piece of material that is sized and shaped to fit into the space underneath the conjunctiva and attach to the sclera. Thus, the synthetic flap 200 is used in place of the scleral flap cut that is conventionally used in trabeculectomy procedures.

The synthetic flap 200 includes a first set of edges 208a, 208b that extend vertically. The first set of edges 208a, 208b may have a length 202 within a range of about 3 to 7 millimeters. In some examples, the first set of edges 208a, 208b may have a length of about 5 millimeters. Other ranges are contemplated. The synthetic flap 200 also includes a second set of edges 210a, 210b that extend horizontally. The second set of edges 210a, 210b may also have a length 204 within a range of about 3 to 7 millimeters. In some examples, the second set of edges 210a, 210b may have a length of about 5 millimeters. Other ranges are also contemplated.

The synthetic flap 200 may have a thickness 218 within a range of about 0.5 to 1.5 millimeters at the center 220 of the synthetic flap 200, as measured from an inner side 212 to an outer side 214. In one example, the thickness 218 is about 1 millimeter. The outer side 214 of the synthetic flap 200 may be contoured such that the thickness 218 tapers towards the second set of edges 210a, 210b. In some examples, the outer side 214 of the synthetic flap 200 is also contoured such that the thickness tapers towards the first set of edges 208a, 208b as well. The contouring allows the synthetic flap 200 to fit comfortably within the space between the conjunctiva and the sclera.

In some examples, the synthetic flap 200 may be made of a polymer material such as silicone. In some examples, the synthetic flap 200 may be made of an anti-fibrotic material. Such material may reduce scarring. In some examples, the synthetic flap 200 may be made of a non-anti-fibrotic material and an anti-fibrotic coating may be applied to the inner side 212 of the synthetic flap 200. The synthetic flap 200 is an implant device that is designed to be inserted into the eye for an extended period of time. In other words, the synthetic flap resides within the eye for weeks, months, or years after being inserted by a surgeon.

In the present example, the synthetic flap 200 includes an attachment feature 216 extending along the length of one of the edges 210a. The attachment feature 216 is used to connect the synthetic flap 200 to the patient's sclera. In some examples, the attachment feature 216 is an adhesive. It may extend across the inner side 212 in a line adjacent on of the edges. In some examples, the attachment feature 216 is a textured surface designed to stick to the sclera. In some examples, the attachment feature 216 may be set of perforations that allow the synthetic flap 200 to be sutured to the sclera by a running suture.

While the synthetic flap 200 illustrated in FIG. 2 is substantially square-shaped, other shapes are contemplated. For example, the synthetic flap may be substantially rectangular, triangular, or some other polygonal shape with the attachment feature placed along one or more sides of the flap. Some implementations of the synthetic flap may be substantially circular, oval, or may lack defined angled corners, with the attachment feature placed partially along the perimeter of the synthetic flap.

Figure 3:
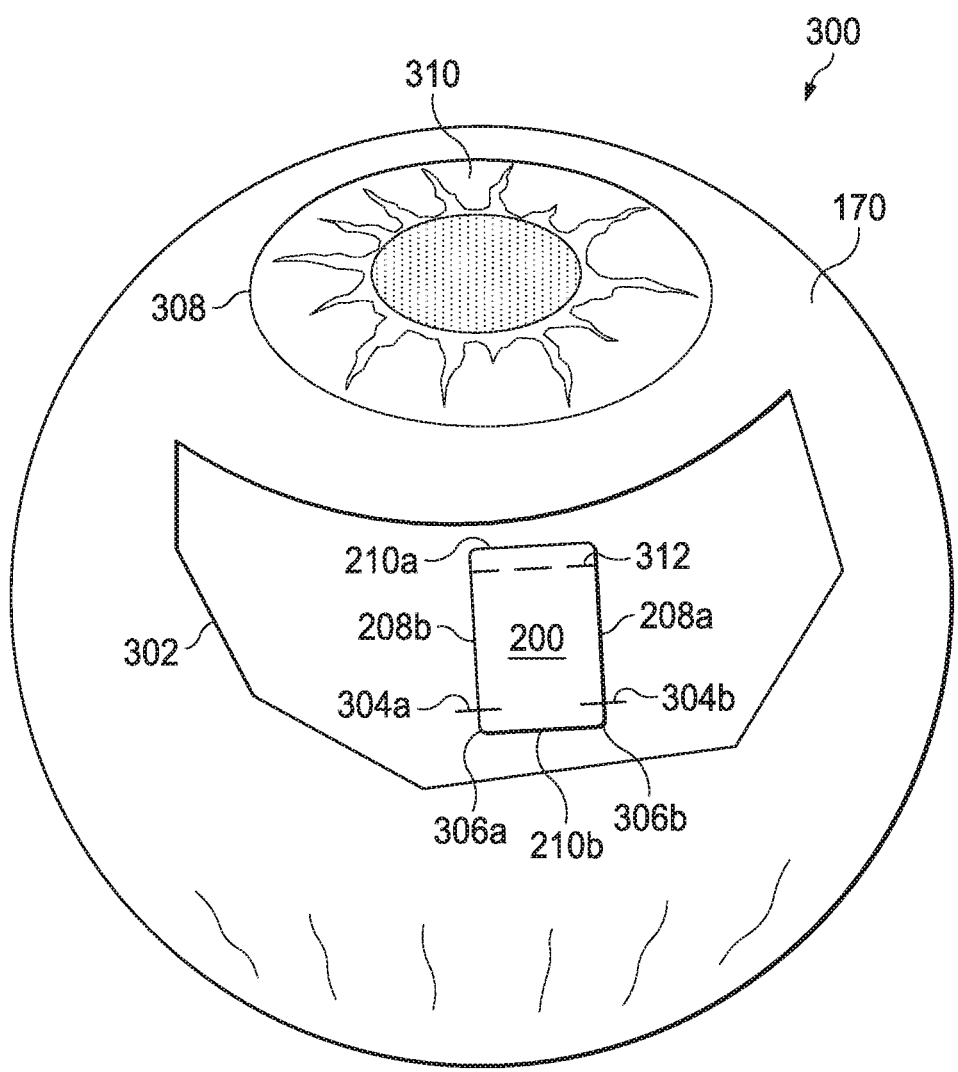
FIG. 3 is a diagram showing illustrative placement of the synthetic flap on a patient's eye according to one example of principles described herein.

FIG. 3 is a diagram showing illustrative placement of the synthetic flap 200 on a patient's eye 300. FIG. 3 illustrates a conjunctival incision 302 formed near the limbus 308. The limbus 308 is the border between the cornea 310 and the sclera 170. As described above, the conjunctival incision 302 creates a space between the conjunctiva 180 (FIG. 1) and the sclera 170. The synthetic flap 200 may then be inserted into that space. The synthetic flap 200 is inserted such that the edge 210a having the attachment feature (e.g., 216, FIG. 2) is placed close to the limbus 308. In the present example, the edge 210a is attached to the sclera 170 through use of a running suture 312.

In some examples, the corners 306a, 306b of the synthetic flap 200 that are opposite of the edge 210a may also be connected to the sclera 170. In the present example, the corners 306a, 306b are attached to the sclera by sutures 304a, 304b. Other mechanisms for attaching the corners 306a, 306b to the sclera 170, such as adhesives or textured surfaces, are contemplated as well.

Figure 4:
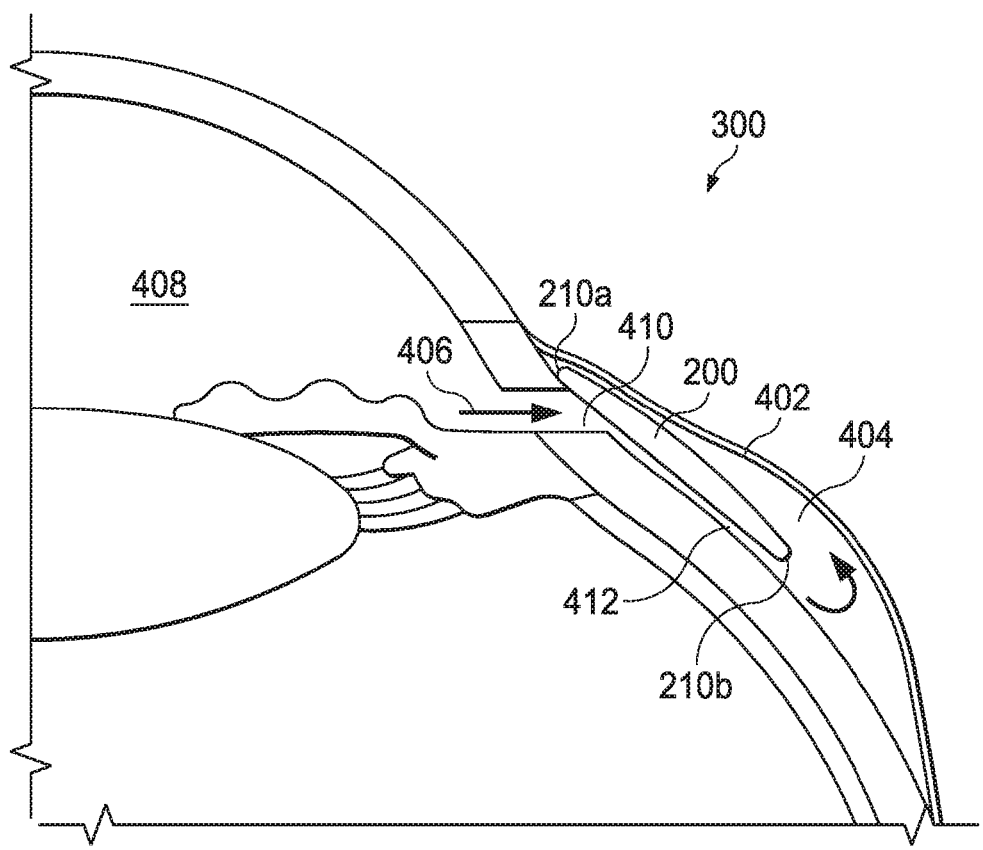
FIG. 4 is a diagram showing a cross-sectional view of the synthetic flap on the patient's eye according to one example of principles described herein.

FIG. 4 is a diagram showing a cross-sectional view of the synthetic flap 200 on a portion of the patient's eye. According to the present example, a scleral tunnel 410 is formed underneath the synthetic flap 200. The scleral tunnel 410 may be positioned adjacent the edge 210a of the synthetic flap 200 that is attached to the sclera 170. The scleral tunnel 410 thus provides a passageway between the anterior chamber 408 and the space 412 underneath the synthetic flap 200. Fluid from the anterior chamber 408 may then flow through the scleral tunnel 410 along direction 406. The fluid may then flow through the space 412 underneath the synthetic flap 200 and into the space 404 between the conjunctiva 402 and the sclera 170. This space 404 may be referred to as the bleb site.

Flow of fluid from the anterior chamber 408 to the bleb site 404 may be controlled by attaching additional portions of the synthetic flap 200 to the sclera 170. For example, as described above, the corners (e.g. 306a, 306b) or edges of the synthetic flap opposite the attached edge may be sutured to the sclera 170. This increases the flow resistance between the anterior chamber 408 and the bleb site 404. To provide additional flow resistance, more of the synthetic flap 200 may be attached to the sclera 170. To reduce flow resistance, less of the synthetic flap 200 may be attached to the sclera 170.

Figure 5:
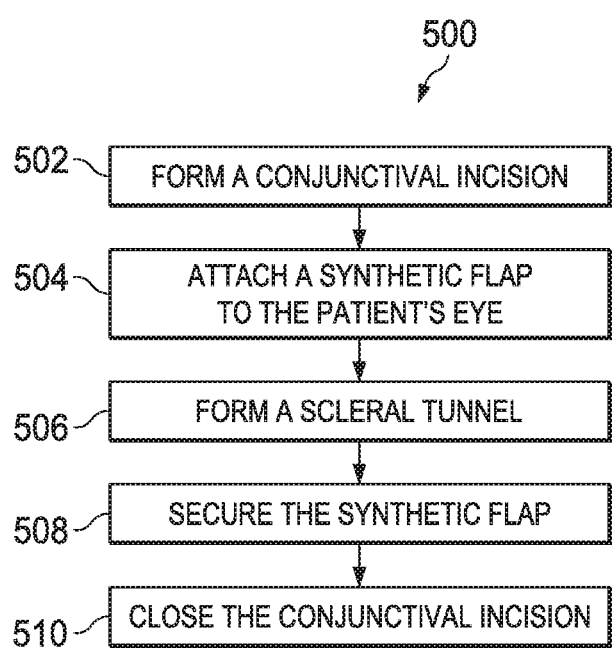
FIG. 5 is a flowchart showing an illustrative method of placing the synthetic flap on the patient's eye according to one example of principles described herein.

FIG. 5 is a flowchart showing an illustrative method 500 of placing the synthetic flap 200 on the patient's eye. According to the present example, at block 502, a conjunctival incision is formed. The conjunctival incision creates a space between the conjunctiva and the sclera. As described above, this space is used as a bleb site. Aqueous humor fluid from the anterior chamber gets drained to the bleb site. From there, the aqueous humor fluid may be absorbed by the patient's anatomy.

At block 504, the synthetic flap (e.g., 200, FIG. 2) is attached to the sclera. The synthetic flap may include an attachment feature that is used to secure one edge of the synthetic flap to the sclera. This edge may be placed near the limbus. Attaching the synthetic flap to the patient's eye may be performed in a variety of manners based on the type of attachment feature used by the synthetic flap. For example, if the attachment feature is an adhesive or textured surface, attaching the synthetic flap involves positioning the synthetic flap and then pressing the attachment feature against the eye, thereby causing it to stick. If the attachment technique involves suturing, then attaching the synthetic flap involves positioning the synthetic flap and then creating a running suture to connect the synthetic flap to the sclera.

At block 506, the scleral tunnel is formed. The scleral tunnel is formed underneath the synthetic flap. The scleral tunnel may be formed at a location near or adjacent to the edge of the synthetic flap that is attached to the sclera. Forming the scleral tunnel may be done in a variety of manners. In one example, a puncturing tool may be used to form the scleral tunnel. In some examples, a knife or scalpel may be used to form the scleral tunnel. Other techniques for forming the scleral tunnel are contemplated as well.

In some examples, at block 508, after the scleral tunnel is formed, the synthetic flap may be further secured to the sclera in order to provide the desired flow resistance. For example, the corners of the synthetic flap opposite the attached edge may be sutured or otherwise secured to the sclera. In some examples, the entire side edges (e.g., 208a, 208b) may be secured to the sclera. The degree to which the synthetic flap is secured to the sclera after the scleral tunnel has been formed may be patient specific and based on a surgeon's judgment.

At block 510, the conjunctival incision is closed. The conjunctival incision may be closed, for example, by suturing. Closing the conjunctival incision closes the space (e.g., 404, FIG. 4) between the sclera and the conjunctiva. This prevents the aqueous humor fluid from leaking out into an external environment. The enclosed space between the sclera on the conjunctiva this creates a bleb site to which the aqueous humor fluid may drain. This may relieve the intraocular pressure within the eye.

As described above, using the synthetic flap as described herein provides various advantages not obtained in conventional surgical procedures. For example, surgeons of varying skill levels may create a consistent, repeatable flow path, making outcomes more predictable. Additionally, the trabeculectomy procedure may be less invasive for the patient. Furthermore, the synthetic flap may be made of an anti-fibrotic material to reduce scarring and prolong the efficacy of the trabeculectomy procedure.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of treating glaucoma, the method comprising: providing a synthetic flap comprising:
    a polymer sheet material sized and shaped to be inserted into a conjunctival incision, the polymer sheet material having (i) a height within a range of 3 millimeters and 7 millimeters; (ii) a width within a range of 3 millimeters and 7 millimeters; (iii) a thickness within a range of 0.5 millimeters to 1.5 millimeters; (iv) an anti-fibrotic material; and (v) an attachment feature extending along a length of an edge of the polymer sheet material, the attachment feature arranged to secure the polymer sheet material to a sclera of a patient's eye;
    forming a conjunctival incision in a patient's eye, the conjunctival incision creating a subconjunctival space between the conjunctiva and the sclera near a limbus of the patient's eye, the conjunctival incision not creating a scleral flap or scleral incision;

placing the synthetic flap within the conjunctival incision;

attaching the synthetic flap on an exterior surface of the sclera within the subconjunctival space created between the conjunctiva and the sclera;

forming a scleral tunnel underneath the synthetic flap, the scleral tunnel extending from said exterior surface of the sclera to an anterior chamber of the patient's eye; and closing the conjunctival incision, wherein attaching the synthetic flap comprises attaching said edge of the polymer sheet material to the sclera utilizing said attachment feature, wherein the scleral tunnel is positioned adjacent said edge of the polymer sheet material, wherein the scleral tunnel is devoid of any synthetic flap or prosthetic components, wherein the synthetic flap creates a consistent, repeatable flow drainage path of aqueous humor fluid from the anterior chamber of the patient's eye, through the scleral tunnel, through a space underneath the synthetic flap, and into the subconjunctival space between the conjunctiva and the sclera.

2. The method of claim 1, further comprising, after forming the scleral tunnel, suturing a corner of the synthetic flap to the sclera.

3. The method of claim 1, wherein the polymer sheet material is contoured.

4. The method of claim 1, wherein the attachment feature comprises a line of adhesive.

5. The method of claim 1, wherein the attachment feature comprises perforations for a running suture.

6. The method of claim 1, wherein the attachment feature comprises a textured edge.

* * * * *